(12) United States Patent
Warrell, Jr.

(10) Patent No.: US 9,428,466 B2
(45) Date of Patent: Aug. 30, 2016

(54) METHODS FOR REDUCING URIC ACID LEVELS USING BARBITURATE DERIVATIVES

(71) Applicant: Raymond P. Warrell, Jr., Westfield, NJ (US)

(72) Inventor: Raymond P. Warrell, Jr., Westfield, NJ (US)

(*) Notice: Subject to any disclaimer, the term of this patent is extended or adjusted under 35 U.S.C. 154(b) by 178 days.

(21) Appl. No.: 14/078,668

(22) Filed: Nov. 13, 2013

(65) Prior Publication Data

US 2015/0133477 A1 May 14, 2015

(51) Int. Cl.
*A61K 31/513* (2006.01)
*C07D 239/60* (2006.01)

(52) U.S. Cl.
CPC ........... *C07D 239/60* (2013.01); *A61K 31/513* (2013.01)

(58) Field of Classification Search
None
See application file for complete search history.

(56) References Cited

U.S. PATENT DOCUMENTS

| | | |
|---|---|---|
| 4,636,508 A | 1/1987 | Brewer et al. |
| 4,762,830 A | 8/1988 | Sturm et al. |
| 4,879,276 A | 11/1989 | Brewer |
| 4,880,811 A | 11/1989 | Warrell, Jr. |

FOREIGN PATENT DOCUMENTS

WO    WO 8810114 A1 * 12/1988 ........... A61K 31/515

OTHER PUBLICATIONS

Muindi et al., In vitro differential metabolism of merbarone by xanthine oxidase and microsomal flavoenzymes: the role of reactive oxygen species, Drug Metabolism and Disposition (1993), 21(3), 410-14.*
STN Document No. 111:225323.*
Supko et al., Characterization of the urinary metabolites of merbarone in cancer patients, Drug Metabolism and Disposition.*
PCT International Search Report and Written Opinion in PCT/US2014/064561, mailed Feb. 27, 2015, 15 pages.
Attia, Sabry, Molecular cytogenetic analysis of chemically induced aneuploidy in germinal and somatic cells of mice: studies with topoisomerase II inhibitors, *Ph.D. Thesis, Technical University of Munich*, Germany 2004, 135 pages.
"Evidence from Studies with Intact Mammalian Cells That Merbarone and bis(Dioxopiperazines)s Are Topoisomerase II Poisons", *Drug and Chemical Toxicology*, vol. 26, No. 1 (Abstract), 2 pgs.
Attia, Sabry M., "Dominant lethal mutations of topoisomerase II inhibitors etoposide and merbraone in male mice: a mechanistic study", *Arch Toxicol* Dec. 30, 2011, 7 pgs.
Attia, S. M. et al., "Etoposide and merbarone are clastogenic and aneugenic in the mouse bone marrow micronucleus test complemented by fluorescence in situ hybridization with the mouse minor satellite DNA probe", *Environmental and Molecular Mutagenesis*, vol. 41 (Abstract) 2003, 3 pgs.
Caulfield, Mark J. et al., "SLC2A9 Is a High-Capacity Urate Transporter in Humans", *PloS Medicine*, vol. 5, Issue 10 Oct. 2008, 1509-1523.
DiMaggio, J. J. et al., "Phase I Clinical and Pharmacological Study of Merbarone1", *Cancer Research 50* Feb. 15, 1990, 1151-1155.
Drake, Fred H. et al., "In Vitro and Intracellular Inhibition of Topoisomerase II by the Antitumor Agent Merbarone", *Cancer Research 49* May 15, 1991, 2578-2583.
Dubchak, Natalie et al., "New and improved strategies for the treatment of gout", *International Journal of Nephrology and Renovascular Disease* 2010, 145-166.
Fortune, John M. et al., "Merbarone Inhibits the Catalytic Activity of Human Topoisomerase IIa by Blocking DNA Cleavage", *The Journal of Biological Chemistry*, vol. 273, No. 28 1998, 17643-17650.
Kemmenoe, Brian H. et al., "Distribution of [2-14C]Merbarone in Mice by Autoradiography of Whole-Body Cryosections1", *Cancer Research 47* Feb. 15, 1987, 1135-1142.
Khelifa, Tayeb et al., "Merbarone, a Catalytic Inhibitor of DNA Topoisomerase II, Induces Apoptosis in CEM Cells through Activation of ICE/CED-3-like Protease", *Molecular Pharmacology*, 55 1999, 548-556.
Kusumoto, Hiroki et al., "Characterization of Novel Human Leukemic Cell Lines Selected for Resistance to Merbarone, a Catalytic Inhibitor of DNA Topoisomerase II1", *Cancer Research 56* Jun. 1, 1996, 2573-2583.
Larsen, Annette K. et al., "Catalytic topoisomerase II inhibitors in cancer therapy", *Pharmacology & Therapeutics*, vol. 99, Issue 2 (Abstract) Aug. 2003, 2 pgs.
Lee, M. H. et al., "A benefit-risk assessment of benzbromarone in the treatment of gout. Was its withdrawal from the market in the best interest of patients?", *Drug Saf. 31(8)* 2008, 643-65.
Machon Z., Dlugosz A., "Antitumor and immunosuppressive activity of Merbarone's analogues and arylidenehydrazinopyrimidines", *Pharmazie 50* (Abstract) Aug. 1995, 1 pg.
Miner, J. N. et al., "RDEA684, a Novel, Potent and Efficacious Inhibitor of Human Urate Transporter, URAT1, with a Favorable Pharmacokinetic Profile, and no Mitochondrial Toxicity", *Annual European Contress of Rheumatology EULAR 2010* 2010, 14 pgs.
Mundi, Josephia F. et al., "In Vitro Differential Metabolism of Merbarone by Xanthine Oxidase and Microsomal Flavoenzymes", *Drug Metabolism and Disposition*, vol. 21, No. 3 Aug. 1, 1991, 410-414.

(Continued)

*Primary Examiner* — Svetlana M Ivanova
(74) *Attorney, Agent, or Firm* — Servilla Whitney LLC

(57) ABSTRACT

Methods for reducing uric acid levels in blood or serum of a subject employing metabolites of merbarone as active agents. Methods for treating or preventing disorders of uric acid metabolism are also provided. The metabolites can be formulated as pharmaceutical compositions comprising the metabolites and a pharmaceutically acceptable carrier for use in these methods.

12 Claims, 1 Drawing Sheet

(56) References Cited

OTHER PUBLICATIONS

Otake, Yoko et al., "Merbarone Induces Activation of Caspase-Activated DNase and Excision of Chromosomal DNA Loops from the Nuclear Matrix", *Molecular Pharmacology*, 69 2006, 1477-1485.

Ranise, Angelo et al., "Synthesis and Antiproliferative Activity of Basic Thioanalogues of Merbarone", *Bioorganic & Medicinal Chemistry 11* 2003, 2575-2589.

Reinders, M. K. et al., "A randomised controlled trial on the efficacy and tolerability with dose escalation of allopurinol 300-600 mg/day versus benzbromarone 100-200 mg/day in patients with gout", Downloaded from ard.bmj.com Jun. 24, 2010, 6 pgs.

Reinders, M. K. et al., "Efficacy and tolerability of urate-lowering drugs in gout: a randomised controlled trial of benzbromarone versus probenecid after failure of allopurinol", Downloaded from ard.bmj.com Jun. 24, 2010, 6 pgs.

Sanchez-Lozada, Laura G. et al., "Treatment with the xanthine oxidase inhibitor febuxostat lowers uric acid and alleviates systemic and glomerular hypertension in experimental hyperuricaemia", *Nephrol Dial Transplant 23* 2008, 1179-1185.

Snyder, Ronald D., "Evidence from Studies with Intact Mammalian Cells That Merbarone and bis(Dioxopiperazine)s Are Topoisomerase II Poisons", *Drug and Chemical Toxicology*, vol. 26, No. 1 2003, 15-22.

Supko, Jeffrey G. et al., "Characterization of the Urinary Metabolites of Merbarone", *Drug Metabolism and Disposition*, vol. 19, No. 1 1990, 263-273.

Tausche, Anne-Kathrin et al., "Gout—Current Diagnosis and Treatment", *Deutsches Arzteblatt International 106 (34-35)* 2009, 549-555.

Warrell, Raymond P. et al., "Induction of Profound Hypouricemia by a Non-Sedating Thiobarbiturate", *Metabolism*, vol. 38, No. 6 Jun. 1989, 550-554.

International Preliminary Report on Patentability in PCT/US2014/064561, dated May 17, 2016, 11 pgs.

\* cited by examiner

US 9,428,466 B2

METHODS FOR REDUCING URIC ACID LEVELS USING BARBITURATE DERIVATIVES

TECHNICAL FIELD

This invention relates to methods for reducing uric acid in blood or serum of a subject employing metabolites of merbarone as active agents.

BACKGROUND

Gout afflicts more than 8 million U.S. subjects, and is associated with chronic elevation of uric acid (UA) in blood. The incidence of this condition has doubled in the past ten years. When UA exceeds solubility limits, it forms crystals that settle into joints and kidney, causing severe pain, destructive arthritis, and kidney failure. Treatment for chronic gout entails extended—if not lifelong—therapy focused on reducing UA production or increasing its excretion. The standard-of-care is allopurinol, a drug that inhibits xanthine oxidase (XO), a key production enzyme. Launched in 2010, Uloric® (febuxostat; Takeda), has similar activity with an improved safety profile. Xanthine oxidase inhibitors are used as initial therapy in more than 90% of gout patients, but the therapeutic target is achieved in less than 50%. The drugs have multiple side effects and hypersensitivity is common.

Since 2000, rapid advances in the biology of proteins known as transporters have presented an array of new drug targets. The enzyme URAT1 is a high capacity renal transporter that reabsorbs most of the UA that is initially filtered into the urine from the blood by the kidney. Inhibitors of certain urate transporters may prevent such reabsorption and thereby increase UA excretion. Several drugs are now known to inhibit URAT1, including benzbromarone (approved but withdrawn by Sanofi in 2003), probenecid, and lesinurad (AstraZeneca), a drug currently in Phase 3 development.

These drugs are all mono-functional. That is, they inhibit only one of the two equilibrium paths that reduce the levels of UA in blood (i.e., decreased production or increased excretion). Allopurinol is an example of a drug that decreases UA production by inhibiting xanthine oxidase, but it has no effect on renal excretion. As expected, allopurinol does not affect the activity of URAT1 or other renal urate transporters. Benzbromarone, lesinurad and probenecid increase UA excretion (i.e., they promote uricosuria) primarily via inhibition of URAT1, but these agents have no effect on UA production, since they have no substantial effect on xanthine oxidase. Since xanthine oxidase inhibition is the principal and primary form of treatment for hyperuricemia, agents that promote uricosuria are typically used second-line and are commonly employed in combination with xanthine oxidase inhibitors rather than as single-agents.

5-carboxanilide derivatives of barbiturates, including merbarone (5-(N-phenylcarboxamido)-2-thio-barbituric acid) have been evaluated as potential cytotoxic anticancer drugs. Subsequently, it was discovered that clinical treatment with merbarone was associated with a marked reduction of UA levels in blood. Despite these discoveries, the cytotoxic activity of merbarone would completely preclude its use as a treatment for chronic lifelong disorders of UA metabolism, since the safety of such use (primarily its carcinogenic potential) would pose a serious risk to other aspects of human health. Such clinical utility would only be possible if the cytotoxic activity could be chemically dissociated from the various hypouricemic activities. However, no non-cytotoxic (or low cytotoxicity) hypouricemic derivatives of merbarone have yet been reported.

The urinary metabolites of merbarone were initially characterized by a team led by one of the inventors (R. P. Warren, Jr.) (see J. J. Dimaggio, et al., 1990. Cancer Res. 50:1151) and by J. G. Supko, et al. (1991. Drug Metabolism and Disposition. 19:263-273). Three of these metabolites were identified as 4'-hydroxymerbarone[1,2,3,4-tetrahydro-6-hydroxy-2-thioxo-4-oxo-N-(4'-hydroxyphenyl)-5-pyrimidinecarboxamide or 5-(N-(4'-hydroxyphenyl)carbamoyl)-2-thioxobarbituric acid], 2-oxo-desthiomerbarone[1,2,3,4-tetrahydro-6-hydroxy-2,4-dioxo-N-phenyl-5-pyrimidinecarboxamide or 5-(N-phenylcarbamoyl)barbituric acid], and 4'-hydroxy-2-oxo-desthiomerbarone[1,2,3,4-tetrahydro-6-hydroxy-2,4-dioxo-N-(4'-hydroxyphenyl)-5-pyrimidinecarboxamide or 5-(N-(4'-hydroxyphenyl)carbamoyl)barbituric acid]. Several minor metabolites were also found, but were not identified.

There exists a compelling need for new drugs than can reduce UA levels in blood and provide better treatment for patients afflicted by gout. Reduction in UA is universally acknowledged as beneficial for patients with gout and other hyperuricemic disorders, and reduced serum UA is accepted by international drug regulatory agencies (e.g., the U.S. Food and Drug Administration (FDA), the European Medicines Agency (EMA), etc.) as an endpoint for commercial drug approval in these diseases. As previously noted, drugs that can overcome the limited clinical activity of xanthine oxidase inhibitors are available or are currently being investigated, but only as "add-ons" for combination use. Heretofore, the use of a single drug with potent bifunctional activity (i.e., to decrease UA production by inhibiting xanthine oxidase and to increase UA excretion by inhibiting a renal urate transporter) and low toxicity has not been possible. It has now been discovered that certain metabolites of merbarone address each of these needs.

SUMMARY

Preliminary investigations by others in the prior art reported that merbarone was a modest inhibitor of xanthine oxidase. However, more recent studies by the inventors have now shown that this effect of merbarone is both minimal and inadequate to support therapeutic use for disorders of uric acid metabolism, even if the drug's cytotoxic activity could have been eliminated. Instead, the inventors have discovered that merbarone is a prodrug for certain (but not all) metabolites that exert highly potent inhibition of xanthine oxidase at concentrations that equal or exceed the potency of allopurinol. Moreover, the inventors have further discovered that merbarone increases urinary UA excretion by inhibiting the URAT1 renal transporter, and that certain (but not all) merbarone metabolites are considerably more potent URAT1 inhibitors than many other pro-uricosuric agents currently in clinical or investigational use. To our knowledge, this bifunctional activity to both inhibit UA production and to reduce UA excretion with a single compound has not been previously described. Lastly, the inventors have also unexpectedly found that certain of these bifunctional metabolites are no longer cytotoxic, or they exhibit sufficiently low cytotoxicity to permit their use for long term treatment of patients with disorders of uric acid metabolism.

A first aspect of the invention relates to methods for reducing uric acid levels in blood or serum of a subject comprising administering one or more of 2-oxo-desthiomerbarone, 4'-hydroxy-2-oxo-desthiomerbarone and 4'-hydroxymerbarone to a subject in need thereof in an amount effective to reduce blood or serum uric acid levels. In a specific embodiment, the methods for reducing uric acid levels in blood or serum of a subject comprise administering 4'-hydroxy-2-oxo-desthiomerbarone, 4'-hydroxymerbarone, or a combination thereof, to a subject in need thereof in an amount effective to reduce blood or serum uric acid levels. A modification of this aspect of the invention related to methods for preventing elevation of uric acid levels in blood or serum of a subject comprising administering one or more of 2-oxo-desthiomerbarone, 4'-hydroxy-2-oxo-desthiomerbarone and 4'-hydroxymerbarone to a subject in need thereof in an amount effective to prevent elevation of blood or serum uric acid levels. In a specific embodiment of this aspect, the methods for preventing elevation of uric acid levels in blood or serum of a subject comprise administering 4'-hydroxy-2-oxo-desthiomerbarone, 4'-hydroxymerbarone, or a combination thereof, to a subject in need thereof in an amount effective to prevent elevation of blood or serum uric acid levels.

In certain embodiments of these methods, one of more of 2-oxo-desthiomerbarone, 4'-hydroxy-2-oxo-desthiomerbarone and 4'-hydroxymerbarone is administered to a subject with gout, hyperuricemia, kidney disease, arthritis, kidney stones, kidney failure, urolithiasis, plumbism, hyperparathyroidism, psoriasis, inborn genetic errors of metabolism, sarcoidosis or cardiovascular disease to reduce uric acid levels. In specific embodiments, the drug(s) are administered to a subject with gout or hyperuricemia to reduce uric acid levels. In other embodiments, 4'-hydroxy-2-oxo-desthiomerbarone, 4'-hydroxymerbarone, or a combination thereof, are administered to a subject with gout, hyperuricemia, kidney disease, arthritis, kidney stones, kidney failure, urolithiasis, plumbism, hyperparathyroidism, psoriasis, inborn genetic errors of metabolism, sarcoidosis or cardiovascular disease to reduce uric acid levels.

In certain embodiments of any of the foregoing methods, one or more of 2-oxo-desthiomerbarone, 4'-hydroxy-2-oxo-desthiomerbarone and 4'-hydroxymerbarone is administered by injection, infusion, intranasal, intrarectal, or oral administration. In other embodiments, 4'-hydroxy-2-oxo-desthiomerbarone, 4'-hydroxymerbarone, or a combination thereof, are administered by injection, infusion, or oral administration.

In certain embodiments of any of the foregoing methods, one or more of 2-oxo-desthiomerbarone, 4'-hydroxy-2-oxo-desthiomerbarone and 4'-hydroxymerbarone is administered in a formulation that enables controlled release. In specific embodiments, the controlled release formulation is an oral controlled release formulation. In other embodiments of any of the foregoing methods, 4'-hydroxy-2-oxo-desthiomerbarone, 4'-hydroxymerbarone, or a combination thereof, are administered in a formulation that enables controlled release.

In certain embodiments of any of the foregoing methods, blood or serum uric acid levels are reduced by at least about 25% compared to blood or serum uric acid levels prior to administration of one or more of 2-oxo-desthiomerbarone, 4'-hydroxy-2-oxo-desthiomerbarone and 4'-hydroxymerbarone. In specific embodiments, blood or serum uric acid levels of the subject are reduced by at least about 50% compared to levels prior to administration. In a specific embodiment, uric acid levels are reduced by about 75% even at daily doses of 1,500 mg/m$^2$/day or less. In alternative embodiments of any of the foregoing methods, blood or serum uric acid levels are reduced by these amounts compared to blood or serum uric acid levels prior to administration of 4'-hydroxy-2-oxo-desthiomerbarone, 4'-hydroxymerbarone, or a combination thereof.

In certain embodiments of any of the foregoing methods, one or more of 2-oxo-desthiomerbarone, 4'-hydroxy-2-oxo-desthiomerbarone and 4'-hydroxymerbarone is administered to the subject up to four times per day, once daily, once, twice or three times per week or once monthly. In other embodiments of any of the foregoing methods, 4'-hydroxy-2-oxo-desthiomerbarone, 4'-hydroxymerbarone, or a combination thereof, are administered to the subject up to four times per day, once daily, once, twice or three times per week or once monthly.

A second aspect of the invention relates to methods for treating a disorder of uric acid metabolism associated with or caused by elevated uric acid in blood or serum comprising administering to a subject in need thereof one or more of 2-oxo-desthiomerbarone, 4'-hydroxy-2-oxo-desthiomerbarone and 4'-hydroxymerbarone in an amount effective to reduce blood or serum uric acid levels or prevent elevation of blood or serum uric acid levels, thereby treating the disorder of uric acid metabolism. One such embodiment relates to methods for treating a disorder of uric acid metabolism associated with or caused by elevated uric acid in blood or serum comprising administering to a subject in need thereof 4'-hydroxy-2-oxo-desthiomerbarone, 4'-hydroxymerbarone, or a combination thereof, in an amount effective to reduce blood or serum uric acid levels, thereby treating the disorder of uric acid metabolism. A second such embodiment relates to methods for treating a disorder of uric acid metabolism associated with or caused by elevation of uric acid in blood or serum comprising administering to a subject in need thereof 4'-hydroxy-2-oxo-desthiomerbarone, 4'-hydroxymerbarone, or a combination thereof, in an amount effective to prevent elevation of blood or serum uric acid levels, thereby treating the disorder of uric acid metabolism. Specific embodiments of these methods for treating a disorder of uric acid metabolism are as described above for reducing uric acid levels in blood or serum.

A further aspect of the invention provides a pharmaceutical composition comprising one or more of 2-oxo-desthiomerbarone, 4'-hydroxy-2-oxo-desthiomerbarone and 4'-hydroxymerbarone and a pharmaceutically acceptable carrier. In a specific embodiment, the pharmaceutical composition comprises 4'-hydroxy-2-oxo-desthiomerbarone, 4'-hydroxymerbarone, or a combination thereof. In a further specific embodiment, 2-oxo-desthiomerbarone is not included in the pharmaceutical composition, i.e., the pharmaceutical composition consists essentially of 4'-hydroxy-2-oxo-desthiomerbarone or 4'-hydroxymerbarone, or a combination thereof.

In certain embodiments of the pharmaceutical composition, the pharmaceutically acceptable carrier is selected from the group consisting of one or more of a solvent, a dispersing agent, a coating, a surfactant, a preservative, an alcohol, a polyol, and an isotonic agent.

In certain embodiments of any of the foregoing pharmaceutical compositions, the composition is formulated for administration by injection, infusion or oral routes.

In certain embodiments of any of the foregoing pharmaceutical compositions, the composition is formulated as a solution, emulsion, capsule, or tablet.

In certain embodiments of any of the foregoing pharmaceutical compositions, the composition is formulated for controlled release of the 2-oxo-desthiomerbarone, 4'-hydroxy-2-oxo-desthiomerbarone and/or 4'-hydroxymerbarone.

DETAILED DESCRIPTION

Figure 1A:
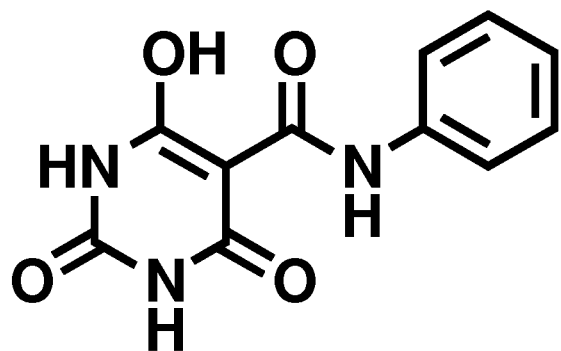
FIG. 1A illustrates the chemical structure of 2-oxo-desthiomerbarone.

Before describing several exemplary embodiments of the invention, it is to be understood that the invention is not limited to the details of construction or process steps set forth in the following description. The invention is capable of other embodiments and of being practiced or being carried out in various ways.

Reference throughout this specification to "one embodiment," "certain embodiments," "one or more embodiments" or "an embodiment" means that a particular feature, structure, material, or characteristic described in connection with the embodiment is included in at least one embodiment of the invention. Thus, the appearances of the phrases such as "in one or more embodiments," "in certain embodiments," "in one embodiment" or "in an embodiment" in various places throughout this specification are not necessarily referring to the same embodiment of the invention. Furthermore, the particular features, structures, materials, or characteristics may be combined in any suitable manner in one or more embodiments.

As used herein, the term "bifunctional" with respect to disclosed compounds means that the compound inhibits both a renal transporter, including but not limited to URAT1, and xanthine oxidase. The potency of inhibition of either target may vary, but in general an IC50 of less than about 100 µM for both xanthine oxidase and a renal transporter such as URAT1 is considered bifunctional. An IC50 of less than about 50 µM for both xanthine oxidase and URAT1 is considered a particularly active bifunctional compound, and an IC50 of less than 10 µM is considered a highly potent bifunctional compound.

As used herein, the term "monofunctional" with respect to disclosed compounds means that the compound inhibits either a renal transporter, including but not limited to URAT1, or xanthine oxidase, but not both. The potency of inhibition of single target may vary, but in general an IC50 of greater than about 100 µM for one of xanthine oxidase or URAT1, and an IC50 of less than about 100 µM for the other of xanthine oxidase or URAT1, is considered monofunctional. An IC50 of less than about 50 µM for one of xanthine oxidase or URAT1, and an IC50 of greater than about 100 µM for the other of xanthine oxidase or URAT1, is considered a particularly active monofunctional compound. An IC50 of less than about 10 µM for one of xanthine oxidase or URAT1, and an IC50 of greater than about 100 µM for the other of xanthine oxidase or URAT1, is considered a highly potent monofunctional compound.

As used herein, the term "treatment" refers to reducing elevated uric acid levels in blood or serum, preferably by reducing levels to the normal, low-normal or sub-normal range, with an overall goal of relieving symptoms and/or preventing recurrences of active disease. For example, a typical "therapeutic target" for treatment of elevated serum uric acid is a level≤6.0 mg/dL. "Elevated" uric acid levels generally refers to high-normal and above-normal uric acid levels, as long-term elevated levels can result in conditions that require additional treatment.

As used herein, the term "preventing" elevation of uric acid levels in blood or serum refers to maintaining normal or therapeutically acceptable uric acid levels in blood or serum in a subject who would otherwise experience an increase in uric acid levels, with an overall goal of preventing development or recurrence of symptoms and/or preventing recurrences of active disease. It will be appreciated that prevention of elevation of uric acid levels is a goal of the maintenance therapy discussed below.

Figure 1B:
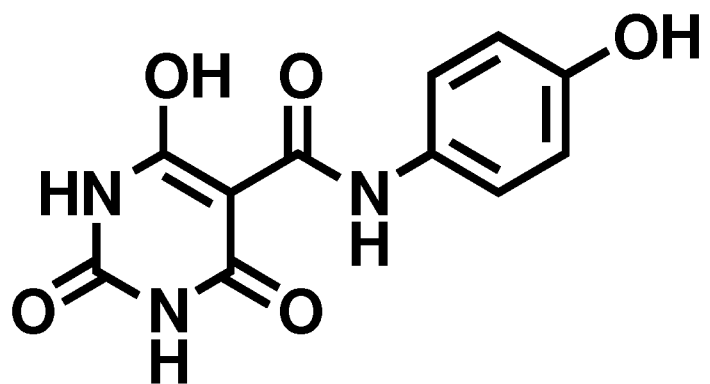
FIG. 1B illustrates the chemical structure of 4'-hydroxy-2-oxo-desthiomerbarone.
Figure 1C:
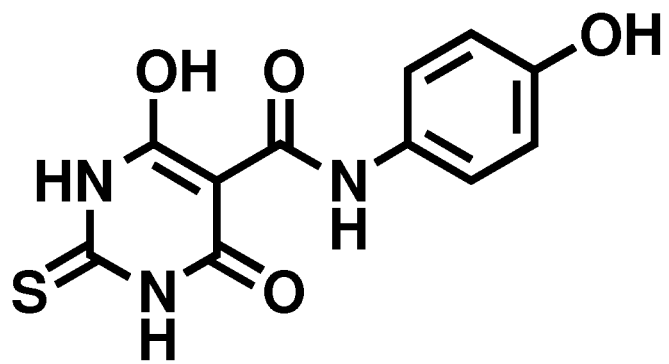
FIG. 1C illustrates the chemical structure of 4'-hydroxymerbarone.

The chemical names 2-oxo-desthiomerbarone, 4'-hydroxy-2-oxo-desthiomerbarone and 4'-hydroxymerbarone are used herein in most instances to identify the compounds used in the methods of the invention. It is to be understood that alternative chemical names may also be used in this application and in the art, and that the terminology used in this application is intended to encompass these alternative chemical names for the identified compound(s). For example, 2-oxo-desthiomerbarone is also known as 1,2,3,4-tetrahydro-6-hydroxy-2,4-dioxo-N-phenyl-5-pyrimidinecarboxamide or 5-(N-phenylcarbamoyl)barbituric acid (FIG. 1A); 4'-hydroxymerbarone is also known as 1,2,3,4-tetrahydro-6-hydroxy-2-thioxo-4-oxo-N-(4'-hydroxyphenyl)-5-pyrimidinecarboxamide or 5-(N-(4'-hydroxyphenyl)carbamoyl)-2-thioxobarbituric acid (FIG. 1C), and; 4'-hydroxy-2-oxo-desthiomerbarone is also known as 1,2,3,4-tetrahydro-6-hydroxy-2,4-dioxo-N-(4'-hydroxyphenyl)-5-pyrimidinecarboxamide, or 5-(N-(4'-hydroxyphenyl)carbamoyl)barbituric acid (FIG. 1B).

The chemical names of the metabolites of merbarone and their chemical structures, as shown and described herein, are also intended to encompass any and all tautomers of these compounds.

Although the existence of 2-oxo-desthiomerbarone, 4'-hydroxy-2-oxo-desthiomerbarone and 4'-hydroxymerbarone as metabolites of merbarone has previously been recognized, it was not previously known that they have any particular uses or advantages for reducing uric acid levels in blood or serum. It has now been unexpectedly found that these compounds meet certain needs in the therapeutic field of reduction of uric acid levels in blood and treatment of disorders of uric acid metabolism that are associated with, or caused by, elevated uric acid levels in blood or serum. 2-oxo-desthiomerbarone has been found to be a monofunctional inhibitor of URAT1 that is more potent than the parent compound merbarone, although it retains cytotoxicity. 4'-hydroxy-2-oxo-desthiomerbarone has unexpectedly been found to be a particularly active bifunctional inhibitor of both URAT1 and xanthine oxidase. It is more potent than allopurinol in inhibition of xanthine oxidase and more potent than merbarone in inhibition of URAT1, with the additional advantage of being substantially non-cytotoxic. 4'-hydroxymerbarone has also been found to be a particularly active bifunctional inhibitor of both URAT1 and xanthine oxidase. Although the URAT1 inhibition of 4'-hydroxymerbarone is somewhat less than merbarone, its xanthine oxidase inhibition is higher than 4'-hydroxy-2-oxo-desthiomerbarone and substantially higher than allopurinol. 4'-hydroxymerbarone is also substantially non-cytotoxic.

The improved biological activity profile of the metabolites of merbarone and their potency make these compounds useful new drugs for reducing uric acid levels in blood, and for treating disorders of uric acid metabolism that are associated with, or caused by, elevated uric acid levels in blood or serum, including gout. Of particular significance is the advantage that the bifunctional compounds can be used effectively as monotherapy for reducing uric acid levels in blood, for treating disorders of uric acid metabolism, and specifically for treating gout. In addition, the non-cytotoxic metabolites minimize safety concerns and are therefore more suitable for long-term administration than merbarone.

In a first aspect, the invention provides methods for reducing uric acid levels in the blood or serum of a subject comprising administering one or more of 2-oxo-desthiomerbarone, 4'-hydroxy-2-oxo-desthiomerbarone and 4'-hydroxymerbarone to the subject in an amount effective to reduce blood or serum uric acid levels. Typically, one or more of 2-oxo-desthiomerbarone, 4'-hydroxy-2-oxo-desthiomerbarone and 4'-hydroxymerbarone (for example, 4'-hydroxy-2-oxo-desthiomerbarone, 4'-hydroxymerbarone or a combination thereof) will be administered when the level of uric acid in the blood of the subject is elevated, i.e., in the upper range of normal or above normal levels. One skilled in the art would further recognize that continued administration after normal uric acid levels are achieved is also contemplated in order to maintain uric acid levels within the normal range and to reduce the overall body burden of uric acid that may have occurred due to previously sustained hyperuricemia. Accordingly, methods for preventing elevation of uric acid levels in blood or serum are also an aspect of the invention. Normal uric acid levels in blood are generally in the range of 4.3 mg/dL to 8.0 mg/dL. In certain embodiments, one or more of 2-oxo-desthiomerbarone, 4'-hydroxy-2-oxo-desthiomerbarone and 4'-hydroxymerbarone (for example, 4'-hydroxy-2-oxo-desthiomerbarone, 4'-hydroxymerbarone or a combination thereof) is administered to a subject with a blood uric acid level of at least about 6 mg/dL. Administration may continue until a blood uric acid level of about 6.0 mg/dL or less is reached; however, it is generally considered to be beneficial to maintain uric acid levels below this target in patients with disorders of uric acid metabolism.

In certain embodiments, the invention provides methods of treating a disorder of uric acid metabolism caused by, or associated with, elevated uric acid levels in blood or serum (hyperuricemia). The method of treating such disorders comprises administering one or more of 2-oxo-desthiomerbarone, 4'-hydroxy-2-oxo-desthiomerbarone and 4'-hydroxymerbarone (for example, 4'-hydroxy-2-oxo-desthiomerbarone, 4'-hydroxymerbarone or a combination thereof) to a subject in need thereof in an amount effective to reduce serum uric acid levels, thereby treating the disorder of uric acid metabolism in the subject. These disorders are associated with, or caused by, elevated uric acid levels in blood or serum which are in the upper range of normal or above normal, and include gout, hyperuricemia, kidney disease, arthritis, kidney stones, kidney failure, urolithiasis, plumbism, hyperparathyroidism, psoriasis, inborn genetic errors of metabolism, sarcoidosis and cardiovascular disease. These drugs are particularly useful for treating gout and kidney disease (including acute uric acid nephropathy, chronic urate nephropathy, and uric acid nephrolithiasis). In addition, treatment of some cancers with chemotherapy leads to the release of large amounts of uric acid into the blood, which can damage the kidneys. Chemotherapy-induced hyperuricemia may also be treated, prevented or ameliorated according to the methods of the invention. Administration of one or more of 2-oxo-desthiomerbarone, 4'-hydroxy-2-oxo-desthiomerbarone and 4'-hydroxymerbarone (for example, 4'-hydroxy-2-oxo-desthiomerbarone, 4'-hydroxymerbarone or a combination thereof) to a subject with hyperuricemia, such as a subject suffering from gout, kidney disease, or a risk if inducing elevated uric acid levels due to chemotherapy, treats, prevents or ameliorates these disorders by reducing uric acid levels in blood, or preventing or controlling their level of increase. In specific embodiments, the disorder of uric acid metabolism treated by administration of one or more of 2-oxo-desthiomerbarone, 4'-hydroxy-2-oxo-desthiomerbarone and 4'-hydroxymerbarone is gout.

The dose of one or more of 2-oxo-desthiomerbarone, 4'-hydroxy-2-oxo-desthiomerbarone and 4'-hydroxymerbarone (for example, the dose of 4'-hydroxy-2-oxo-desthiomerbarone, 4'-hydroxymerbarone or a combination thereof) administered to the subject may be any dose sufficient to achieve a desired reduction in uric acid levels in blood or serum over the time-course of administration. In certain embodiments, a daily dose of about 20 to about 1,500 mg/m$^2$/day is administered. In other embodiments, a daily dose of about 20 to about 500 mg/m$^2$/day, about 20 to about 250 mg/m$^2$/day, about 20 to about 150 mg/m$^2$/day or about 20 to about 100 mg/m$^2$/day is administered. In other embodiments, a daily dose of about 50 to about 1,500 mg/m$^2$/day is administered. In other embodiments, a daily dose of about 50 to about 500 mg/m$^2$/day, about 50 to about 150 mg/m$^2$/day, about 50 to about 100 mg/m$^2$/day, or about 20 to about 100 mg/m$^2$/day is administered.

In certain embodiments of any of the foregoing methods, one or more of 2-oxo-desthiomerbarone, 4'-hydroxy-2-oxo-desthiomerbarone and 4'-hydroxymerbarone (for example, 4'-hydroxy-2-oxo-desthiomerbarone, 4'-hydroxymerbarone or a combination thereof) is administered to the subject parenterally, intraperitoneally, intravenously, intranasally, intrarectally, or orally. Particularly useful routes of administration include injection, infusion, or oral administration. The amount of the drug administered per dose is an amount sufficient to achieve a reduction in uric acid levels in blood or serum, to prevent elevation of uric acid levels in blood or serum, or to treat or prevent a disorder of uric acid metabolism over the course of therapy. One skilled in the art will recognize that individualization of dosage based on a patient's body composition or his/her hypouricemic response to treatment may be medically necessary or desirable.

The drug(s) may be administered to the subject either intermittently or continuously over a period of time in order to achieve the desired reduction in uric acid levels in blood or serum, or to treat a disorder of uric acid metabolism. For example, doses may be administered intermittently several times per day, or at daily, once, twice or three times per week, or monthly intervals. In a specific example, one or more of 2-oxo-desthiomerbarone, 4'-hydroxy-2-oxo-desthiomerbarone and 4'-hydroxymerbarone may be administered to the subject by continuous intravenous infusion over 24 hours for about five days. Alternatively, one or more of 2-oxo-desthiomerbarone, 4'-hydroxy-2-oxo-desthiomerbarone and 4'-hydroxymerbarone may be administered to the subject by intravenous infusion over about 1 hour to about 5 hours for about five days. In a specific example, one or more of 2-oxo-desthiomerbarone, 4'-hydroxy-2-oxo-desthiomerbarone and 4'-hydroxymerbarone may be administered to the subject by intravenous infusion over about 10 minutes for about five days. In further specific embodiments, one or more of 2-oxo-desthiomerbarone, 4'-hydroxy-2-oxo-desthiomerbarone and 4'-hydroxymerbarone may be administered to the subject by daily bolus injections for about five days. Any of these administration protocols may also be applied for administration of 4'-hydroxy-2-oxo-desthiomerbarone, 4'-hydroxymerbarone or a combination thereof. The period of time of administration in any of the foregoing protocols may be modified to achieve the desired reduction in uric acid levels, including about 2 days, about 3 days, about 4 days, about one week or about two weeks of administration, and these treatments may be repeated at intervals of every two to every 10 weeks.

In addition to continuous intravenous infusion or bolus injection, one or more of 2-oxo-desthiomerbarone, 4'-hydroxy-2-oxo-desthiomerbarone and 4'-hydroxymerbarone (including 4'-hydroxy-2-oxo-desthiomerbarone, 4'-hydroxymerbarone or a combination thereof) may be administered to the subject orally. In this embodiment, an oral dose in amounts as described above may be administered in one, two, three or four administrations per day for 1, 2, 3, 4, or 5 days to achieve the desired reduction in uric acid levels. In further embodiments, the oral dose as described above may be administered once per day, or in one, two, three or four administrations per day for one week or two weeks, to achieve the desired reduction in uric acid levels.

It will be appreciated that a subject in need of reduced levels of uric acid in blood or serum, or in need of treatment of a disorder of uric acid metabolism, will be treated more aggressively initially to achieve the desired reduction in uric acid levels. Following initial therapy and reduction of uric acid levels to normal or sub-normal levels, the subject may be further treated over a period of time, or over a lifetime, to maintain normal or sub-normal levels of uric acid in blood or serum and prevent elevation of uric acid levels subsequent to the initial treatment. The maintenance or preventive protocol may comprise reduced dosages and/or less frequent administration of one or more of 2-oxo-desthiomerbarone, 4'-hydroxy-2-oxo-desthiomerbarone and 4'-hydroxymerbarone (or of 4'-hydroxy-2-oxo-desthiomerbarone, 4'-hydroxymerbarone or a combination thereof) as necessary or desired to maintain normal or sub-normal uric acid levels in blood or serum. For example, in a maintenance protocol the drug(s) may be administered daily, weekly or monthly. The initial reduction of uric acid levels from above normal or high normal to normal or sub-normal, and maintenance of normal or sub-normal uric acid levels are both features included in treatment of a disorder of uric acid metabolism. It is anticipated that in certain embodiments, a typical patient will require daily treatment of varying duration, and that such daily treatment will be provided intermittently for life or for extended periods.

In certain embodiments of any of the foregoing methods, blood or serum uric acid levels of the subject are reduced by at least 25% compared to uric acid levels prior to administration of one or more of 2-oxo-desthiomerbarone, 4'-hydroxy-2-oxo-desthiomerbarone and 4'-hydroxymerbarone. In certain further embodiments, blood or serum uric acid levels of the subject are reduced by 50% or more compared to levels prior to administration. In a specific embodiment, uric acid levels are reduced by about 75% even at daily doses of 500 mg/m$^2$/day or less.

In a second aspect of the invention methods are provided for treating a disorder of uric acid metabolism associated with, or caused by, elevated uric acid in blood or serum comprising administering to a subject in need thereof one or more of 2-oxo-desthiomerbarone, 4'-hydroxy-2-oxo-desthiomerbarone and 4'-hydroxymerbarone (for example, 4'-hydroxy-2-oxo-desthiomerbarone, 4'-hydroxymerbarone or a combination thereof) in an amount effective to reduce blood or serum uric acid levels, thereby treating the disorder of uric acid metabolism. Specific embodiments of the methods for treating a disorder of uric acid metabolism relating to dosing, routes of administration, initial therapy and maintenance therapy are as described above for reducing uric acid levels in blood or serum. The initial reduction in uric acid levels is typically rapid, and often occurs within 1-3 days. Upon reduction in uric acid levels to normal or sub-normal levels, continued maintenance or preventive therapy results in a detectable improvement in at least one symptom of elevated uric acid, for example reduced inflammation, reduced pain, slowing of development of deformities, reduced development of kidney stones, or improvement in cardiovascular disease. One skilled in the art will recognize that prevention of recurrent symptoms due to recurrence of elevated serum uric acid levels, thereby necessitating extended treatment, would be highly desirable to maximize patient benefit.

A further aspect of the invention provides a pharmaceutical composition comprising one or more of 2-oxo-desthiomerbarone, 4'-hydroxy-2-oxo-desthiomerbarone and 4'-hydroxymerbarone and a pharmaceutically acceptable carrier. In an alternative embodiment the pharmaceutical composition comprises 4'-hydroxy-2-oxo-desthiomerbarone, 4'-hydroxymerbarone or a combination thereof. In this embodiment, 2-oxo-desthiomerbarone is not a component of the composition. In certain embodiments of any of the foregoing pharmaceutical compositions, the composition is formulated as a solution or tablet. Solutions or dispersions of the drug(s) can be prepared in water or saline. In certain embodiments of the pharmaceutical composition, the pharmaceutically acceptable carrier is one or more component selected from the group consisting of one or more of a solvent, a dispersing agent, a coating (e.g., lecithin), a surfactant (e.g., hydroxypropylcellulose), a preservative (e.g., paraben, phenol, thimerosal, sorbic acid, chlorobutanol), an emulsion, an alcohol (e.g., ethanol), a polyol (e.g., glycerol, propylene glycol), and an isotonic agent (e.g., sugars, sodium chloride).

In certain embodiments of any of the foregoing pharmaceutical compositions, the composition is formulated for controlled release of the 2-oxo-desthiomerbarone, 4'-hydroxy-2-oxo-desthiomerbarone and 4'-hydroxymerbarone (or 4'-hydroxy-2-oxo-desthiomerbarone, 4'-hydroxymerbarone or a combination thereof). In certain embodiments of any of the foregoing methods, one or more of 2-oxo-desthiomerbarone, 4'-hydroxy-2-oxo-desthiomerbarone and 4'-hydroxymerbarone (for example, 4'-hydroxy-2-oxo-desthiomerbarone, 4'-hydroxymerbarone or a combination thereof) is administered in a form for controlled release. The controlled release compositions may include pharmaceutically acceptable carriers or excipients that delay absorption (e.g., aluminum monostearate, gelatin, natural or synthetic hydrophilic gums). Alternatively, controlled release of the pharmaceutical composition may employ a device such as a pump, implant or transdermal patch.

EXAMPLES

The metabolites, 2-oxo-desthiomerbarone, 4'-hydroxy-2-oxo-desthiomerbarone and 4'-hydroxymerbarone were independently synthesized as described in J. G. Supko, et al. (1991. Drug Metabolism and Disposition. 19:263-273) and fully characterized.

The biological activities of 2-oxo-desthiomerbarone, 4'-hydroxy-2-oxo-desthiomerbarone and 4'-hydroxymerbarone were evaluated in three assays: xanthine oxidase activity, URAT1 activity and the in vitro mouse micronucleus assay (a test for cytotoxicity). Merbarone was similarly evaluated for purposes of comparison. Data for lesinurad and allopurinol were obtained from published experimental data for comparison, and to ensure assay comparability, allopurinol activity in a xanthine oxidase assay was also independently assessed.

Xanthine oxidase inhibition was determined using a standard fluorescence-based assay for xanthine oxidase activity (McHale A, Grimes H, Coughlan M P: Int J Biochem. 10:317-9, 1979) with minor variations. The procedure was internally standardized using allopurinol and DPI as controls for all experiments after determination of their optimal inhibitory concentrations. Experiments on test compounds were performed in triplicate in multi-well plates using 10 concentrations of each compound that ranged over a 3-fold dilution.

URAT1 (SLC22A12) activity was evaluated in a cellular uptake assay using a 96-well plate with stably transfected URAT-1/CHO cells. $^3$H-orotate was used as the test transport agent, which was measured in a liquid scintillation counter, using benzbromarone as a positive control, and DMSO and non-transfected CHO cells as negative controls (Solvo Biotechnology, Boston, Mass.). Over 7 concentrations (range, 0.01 to 150 µM), a semi-log plot (percent relative transport of oratate vs. time) was generated to determine the concentration at which 50% inhibition was observed (i.e., the IC50).

The in vitro mouse micronucleus assay was conducted in CHO-K1 cells seeded in 96-well plates and treated with test compounds for 24 hr (without S9) and for 4 hr (with S9). Cytochalasin B was added after 24 hr, and the cells were incubated for an additional 24 hr, after which the cells were fixed and scored for micronuclei. The assay was run using 6 concentrations in duplicate (62 µM-1000 µM), and data for the highest 5 concentrations that were not cytotoxic were reported. Cellular nuclei and micronuclei were stained, and an automated fluorescent microscopic detection system was used to score micronuclei in approximately 2,000 bi-nucleated cells per concentration.

The results of these three assays are shown in the following Table:

| Compound | URAT1 IC50 (µM ± SEM) | Xanthine Oxidase IC50 (µM) | Mouse Micronucleus |
| --- | --- | --- | --- |
| Merbarone | 5.4 ± 1.0 | 274 | Positive |
| 2-oxo-desthiomerbarone | 1.2 ± 0 | >300 | Positive |
| 4'-hydroxy-2-oxo-desthiomerbarone | 2.6 ± 0.6 | 1.06 | Negative |
| 4'-hydroxymerbarone | 9.4 ± 0.6 | 0.68 | Negative |
| Lesinurad | 52.5 ± 5.9* | >300* | ND |
| Allopurinol | >300* | 2.13 | ND |

*Data taken from publications;
ND = not determined

The results of these assays show that both 2-oxo-desthiomerbarone and 4'-hydroxy-2-oxo-desthiomerbarone are more potent inhibitors of URAT1 than merbarone. 4'-hydroxymerbarone also has a useful level of inhibitory activity against URAT1. The results confirm that neither lesinurad nor allopurinol has any useful level of activity against URAT1.

Both 4'-hydroxy-2-oxo-desthiomerbarone and 4'-hydroxymerbarone are also potent inhibitors of xanthine oxidase, whereas merbarone has essentially no inhibitory effect. 2-oxo-desthiomerbarone, similar to merbarone, is also inactive against xanthine oxidase.

Of particular interest was the finding that 4'-hydroxy-2-oxo-desthiomerbarone and 4'-hydroxymerbarone, in contrast to 2-oxo-desthiomerbarone and merbarone, are not cytotoxic. This is an important and valuable feature for a drug that is intended to be administered to a subject for a long period of time.

Although 2-oxo-desthiomerbarone is monofunctional and retains cytotoxicity, it may still be useful for reducing uric acid levels and treating disorders of uric acid metabolism in short-term therapeutic regimens because it is the most potent inhibitor of URAT1 of the three metabolites, and it is significantly more potent against URAT1 than is lesinurad. As an example, 2-oxo-desthiomerbarone might be considered for short term use to prevent or reduce elevated uric acid levels that may results from administration of cancer chemotherapy.

It was an unexpected finding that certain metabolites of merbarone exhibit bifunctional activity and lack of cytotoxicity, whereas the parent compound is both monofunctional and cytotoxic. Other prior art compounds for reduction of uric acid levels are also monofunctional. Availability of a bifunctional drug for reduction of uric acid levels in blood or serum and treatment of disorders of uric acid metabolism associated with or caused by high uric acid levels represents a significant step forward in treatment of these conditions. Moreover, the availability of a bifunctional drug would enable the use of a clinically potent single agent as first-line treatment for disorders of uric acid metabolism by eliminating the need for standard monofunctional xanthine oxidase inhibitors, which are known to be associated with serious (occasionally fatal) adverse reactions. The increased potency of certain of the metabolites allow reduced dosing while still achieving normal or sub-normal uric acid levels in a subject. The elimination of cytotoxicity provides a safe, long-term, therapeutic regimen.

Although the invention herein has been described with reference to particular embodiments, it is to be understood that these embodiments are merely illustrative of the principles and applications of the present invention. It will be apparent to those skilled in the art that various modifications and variations can be made to the method and apparatus of the present invention without departing from the spirit and scope of the invention. Thus, it is intended that the present invention include modifications and variations that are within the scope of the appended claims and their equivalents.

What is claimed is:

1. A method for reducing or preventing elevated blood or serum uric acid levels in a subject comprising administering to a subject in need thereof 4'-hydroxy-2-oxo-desthiomerbarone:

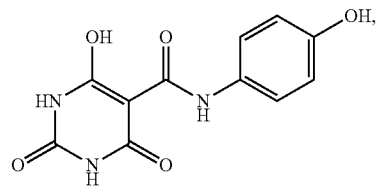

4'-hydroxymerbarone:

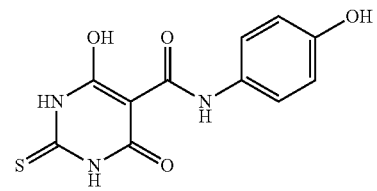

or a combination thereof, in an amount effective to increase renal uric acid excretion and inhibit xanthine oxidase, thereby reducing blood or serum uric acid levels.

2. The method of claim 1, wherein administration is to a subject with gout, hyperuricemia, kidney disease, arthritis, kidney stones, kidney failure, urolithiasis, plumbism, hyperparathyroidism, psoriasis, inborn genetic errors of metabolism, sarcoidosis or cardiovascular disease.

3. The method of claim 2, wherein administration is to a subject with gout or hyperuricemia.

4. The method of claim 1, wherein administration is by injection, infusion, intranasal, intrarectal or oral administration.

5. The method of claim 4, wherein the 4'-hydroxy-2-oxo-desthiomerbarone, 4'-hydroxymerbarone, or a combination thereof, is administered by controlled release.

6. The method of claim 5, wherein 4'-hydroxy-2-oxo-desthiomerbarone, 4'-hydroxymerbarone, or a combination thereof, is administered by oral controlled release.

7. The method of claim 1, wherein blood or serum uric acid levels are reduced by at least 25% compared to blood or serum uric acid levels prior to administration.

8. The method of claim 7, wherein blood or serum uric acid levels are reduced by at least about 50% compared to blood or serum uric acid levels prior to administration.

9. The method of claim 1, wherein administration is once daily; once, twice or three times per week, or; once monthly.

10. The method of claim 1, wherein administration is in an amount of about 20 to about 1500 mg/m$^2$/day.

11. The method of claim 1, wherein administration is in an amount of about 20 to about 500 mg/m$^2$/day.

12. The method of claim 1, further comprising following the reduction in blood or serum uric acid levels with maintenance of normal or sub-normal uric acid levels, or reduction in body burden of uric acid, by administration of similar or reduced dosages and/or less frequent administration of 4'-hydroxy-2-oxo-desthiomerbarone, 4'-hydroxymerbarone, or a combination thereof.

* * * * *